United States Patent
Zhang et al.

(10) Patent No.: US 10,695,514 B2
(45) Date of Patent: Jun. 30, 2020

(54) BREATHING SYSTEM FOR ANESTHESIA MACHINE

(71) Applicant: GENERAL ELECTRIC COMPANY, Schenectady, NY (US)

(72) Inventors: Jiancheng Zhang, Suzhou (CN); Huiqun Cheng, Wuxi (CN); Hui Fang, Wuxi (CN)

(73) Assignee: General Electric Company, Schenectady, NY (US)

( * ) Notice: Subject to any disclaimer, the term of this patent is extended or adjusted under 35 U.S.C. 154(b) by 330 days.

(21) Appl. No.: 15/564,973

(22) PCT Filed: Apr. 7, 2016

(86) PCT No.: PCT/US2016/026470
§ 371 (c)(1),
(2) Date: Oct. 6, 2017

(87) PCT Pub. No.: WO2016/164597
PCT Pub. Date: Oct. 13, 2016

(65) Prior Publication Data
US 2018/0085543 A1   Mar. 29, 2018

(30) Foreign Application Priority Data
Apr. 8, 2015 (CN) .................... 2015 2 0208407 U

(51) Int. Cl.
*A61M 16/01* (2006.01)
*A61M 16/22* (2006.01)
(Continued)

(52) U.S. Cl.
CPC ........ *A61M 16/01* (2013.01); *A61M 16/0078* (2013.01); *A61M 16/0081* (2014.02);
(Continued)

(58) Field of Classification Search
CPC .............. A61M 16/00; A61M 16/0003; A61M 16/0057; A61M 16/0075; A61M 16/0078;
(Continued)

(56) References Cited

U.S. PATENT DOCUMENTS 2,216,183 A * 10/1940 Connell .............. A61M 16/104
128/205.12
5,299,579 A    4/1994 Gedeon et al.
(Continued)

OTHER PUBLICATIONS

International Search Report and Written Opinion for PCT/US2016/026470, dated Jul. 18, 2016, 9 pages.

*Primary Examiner* — Joseph D. Boecker

(57) ABSTRACT

A breathing system for an anesthesia machine is provided, which comprises an operation mode switch, a $CO_2$ canister, a bellows, a patient inspiratory branch and a patient expiratory branch. The operation mode switch comprises a vent communicating with the patient inspiratory branch, a vent communicating with the patient expiratory branch, a vent communicating with the bellows, and a vent communicating with the $CO_2$ canister. The $CO_2$ canister is positioned below the operation mode switch, so as to collect the water flowing through the operation mode switch.

12 Claims, 7 Drawing Sheets

(51) Int. Cl.
*A61M 16/00* (2006.01)
*A61M 16/08* (2006.01)
*A61M 16/20* (2006.01)
*A61M 16/10* (2006.01)

(52) U.S. Cl.
CPC .... *A61M 16/0808* (2013.01); *A61M 16/0891* (2014.02); *A61M 16/20* (2013.01); *A61M 16/22* (2013.01); *A61M 16/208* (2013.01); *A61M 2016/0039* (2013.01); *A61M 2016/0042* (2013.01); *A61M 2016/1025* (2013.01)

(58) Field of Classification Search
CPC .......... A61M 16/0081; A61M 16/0084; A61M 16/009; A61M 16/01; A61M 16/0883; A61M 16/0891; A61M 16/10; A61M 16/104; A61M 16/14; A61M 16/18; A61M 16/20; A61M 16/208; A61M 16/22; A61M 2016/0039; A61M 2016/0042; A61M 2016/1025; A61M 2016/1035
See application file for complete search history.

(56) References Cited

U.S. PATENT DOCUMENTS

| | | | | |
|---|---|---|---|---|
| 5,682,876 | A * | 11/1997 | Pernetti | A61M 16/22 128/202.27 |
| 5,692,494 | A * | 12/1997 | Pernetti | A61M 16/00 128/200.24 |
| 6,571,792 | B1 * | 6/2003 | Hendrickson | A61M 16/08 128/202.22 |
| 6,619,289 | B1 * | 9/2003 | Mashak | A61M 16/0808 128/205.12 |
| 2007/0051367 | A1 | 3/2007 | Mashak et al. | |
| 2009/0165785 | A1 | 7/2009 | Zhang et al. | |
| 2011/0197889 | A1 | 8/2011 | Lahde et al. | |

* cited by examiner

BREATHING SYSTEM FOR ANESTHESIA MACHINE

CROSS-REFERENCE TO RELATED APPLICATIONS

This application is a filing under 35 U.S.C. 371 of international application number PCT/US2016/026470, filed Apr. 7, 2016, which claims priority to Chinese application number ZL 201520208407.3, filed Apr. 8, 2015, the entire disclosures of both are hereby incorporated by reference.

TECHNICAL FIELD

The present disclosure relates to a kind of mechanical equipment, and in particular to a breathing system for anesthesia machine.

BACKGROUND

During use of an anesthesia machine, it is likely that water condensate is produced inside the breathing system due to the moisture caused by the breath of a patient and the effect of soda lime. The water condensate should be discharged as much as possible, in order to prevent from the production of bacteria. In addition, excessive water condensate inside the breathing system can adversely affect the performance and accuracy of measurement sensors, such as gas flow sensors and oxygen concentration sensors. Furthermore, water condensed in the breathing system can increase flow resistance and patient's work of breathing.

An efficient way to remove water condensate in the breathing system is to allow the water condensate to drain and collect in a collecting reservoir or cup at a low position of the breathing system. This solution is low cost and allows a simple approach to collect, and quickly, and regularly, remove water condensate. However if the user forgets to do this, the condensate water will stay inside the respiratory system and the generation of bacteria will be more likely to take place.

Another way to remove moisture from the breathing system is through a tubular heat and moisture exchanger to condense the moisture into water condensate. This is expensive and goes against the miniaturization of the equipment. Similar to the water collecting cup, the tubular heat and moisture exchanger needs to be emptied regularly. Accordingly, it is necessary to provide a novel breathing system for an anesthesia machine, in order to discharge the water condensate therein effectively.

SUMMARY

The exemplary embodiment of the present disclosure provides a breathing system for an anesthesia machine, which comprises an operation mode switch, a $CO_2$ canister, a bellows, a patient inspiratory branch and a patient expiratory branch. The operation mode switch comprises a vent communicating with the patient inspiratory branch, a vent communicating with the patient expiratory branch, a vent communicating with the bellows, and a vent communicating with the $CO_2$ canister. The $CO_2$ canister is positioned below the operation mode switch, so as to collect the water flowing through the operation mode switch.

Other features and aspects will become apparent through the following detailed description, drawings, and claims.

BRIEF DESCRIPTION OF THE DRAWINGS

The present disclosure can be understood better in light of the following description of exemplary embodiments of the present disclosure with reference to the accompanying drawings, in which.

DETAILED DESCRIPTION

Hereinafter, a detailed description will be given for preferred embodiments of the present utility model. It should be pointed out that in the detailed description of the embodiments, for simplicity and conciseness, it is impossible for the Description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as on design, manufacture and production on the basis of the technical contents disclosed in the disclosure are just customary technical means in the art for those of ordinary skilled in the art relating to the contents disclosed in the present utility model, which should not be regarded as insufficient disclosure of the present utility model.

Unless defined otherwise, all the technical or scientific terms used in the Claims and the Description should have the same meanings as commonly understood by one of ordinary skilled in the art to which the present utility model belongs. The terms "first", "second" and the like in the Description and the Claims do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" cover the elements or objects and their equivalents illustrated following the "comprises", "comprising", "includes" and "including", but do not exclude other elements or objects. The term "coupled" or "connected" or the like is not limited to being connected physically or mechanically, nor limited to being connected directly or indirectly.

Figure 1:
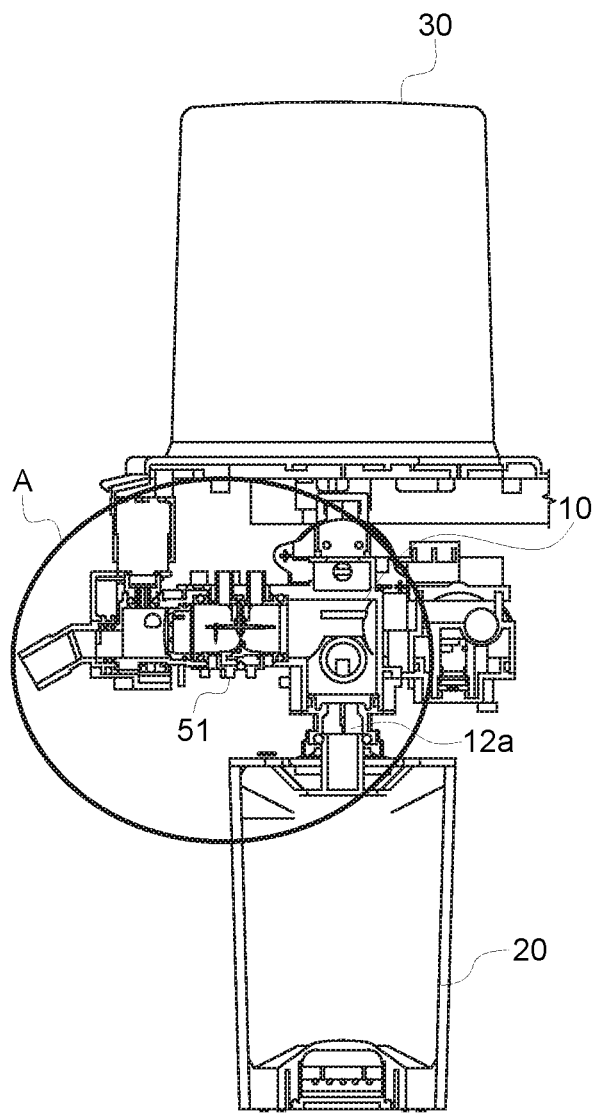
FIGS. 1, 3, 5 and 7 are structural views of a breathing system of an anesthesia machine according to an embodiment of the present disclosure.
Figure 2:
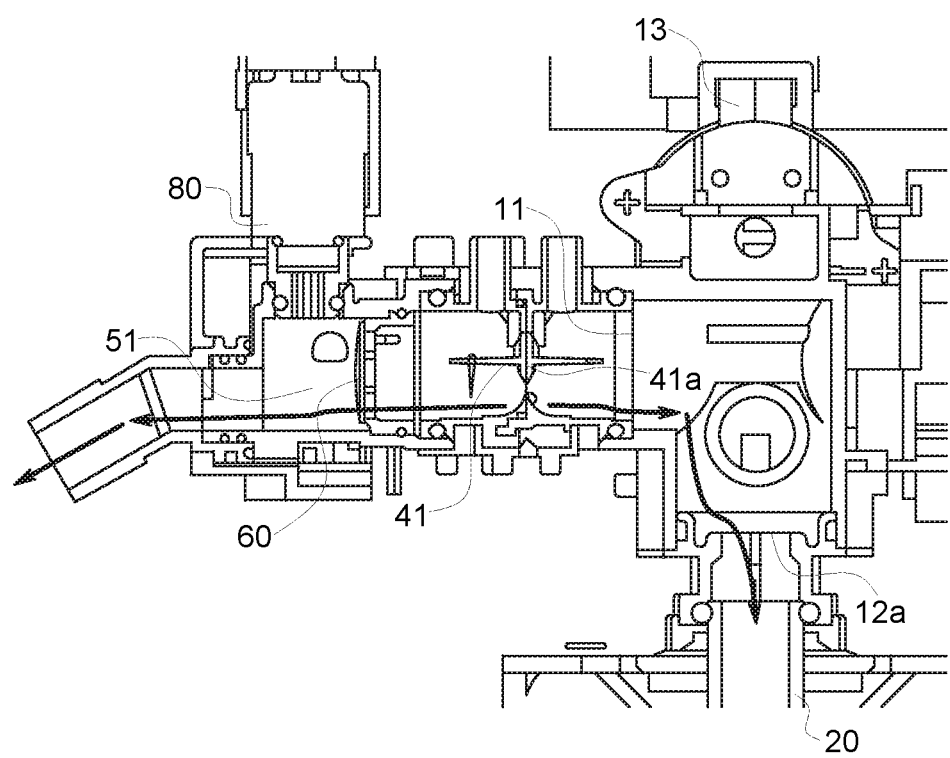
FIG. 2 is an enlarged view of part A in FIG. 1.
Figure 3:
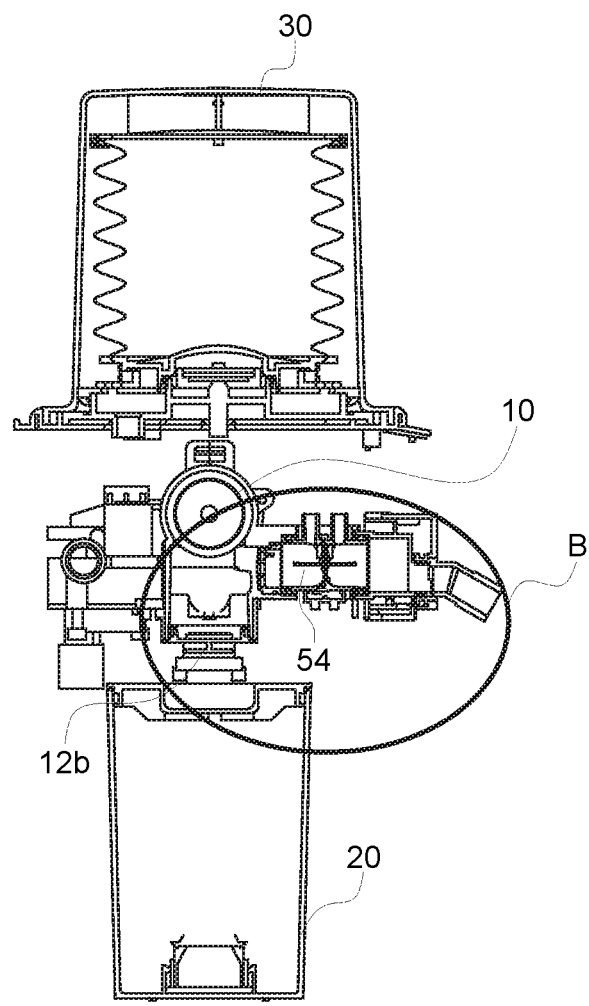
Figure 4:
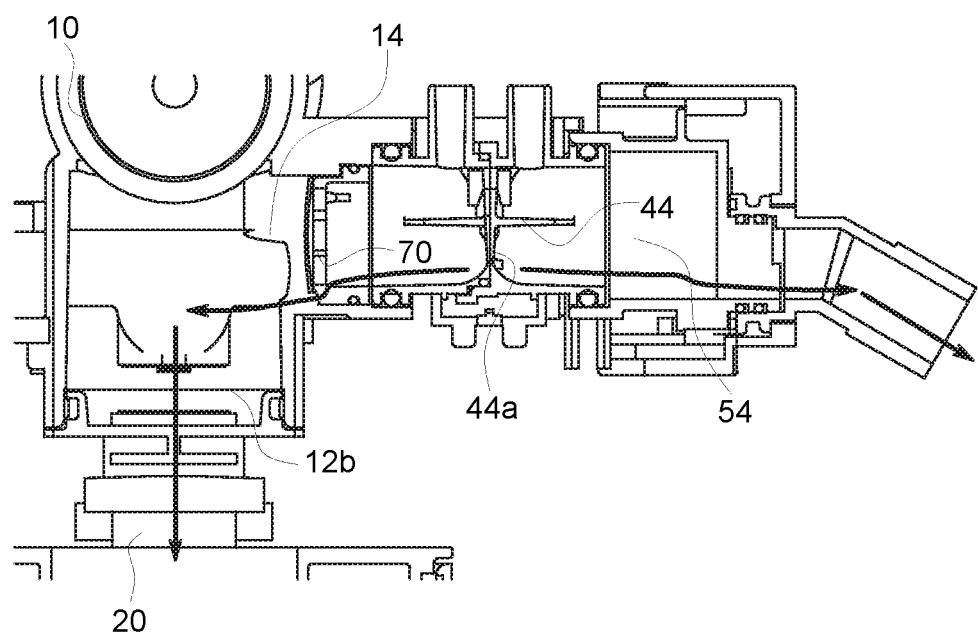
FIG. 4 is an enlarged view of part B in FIG. 3.
Figure 5:
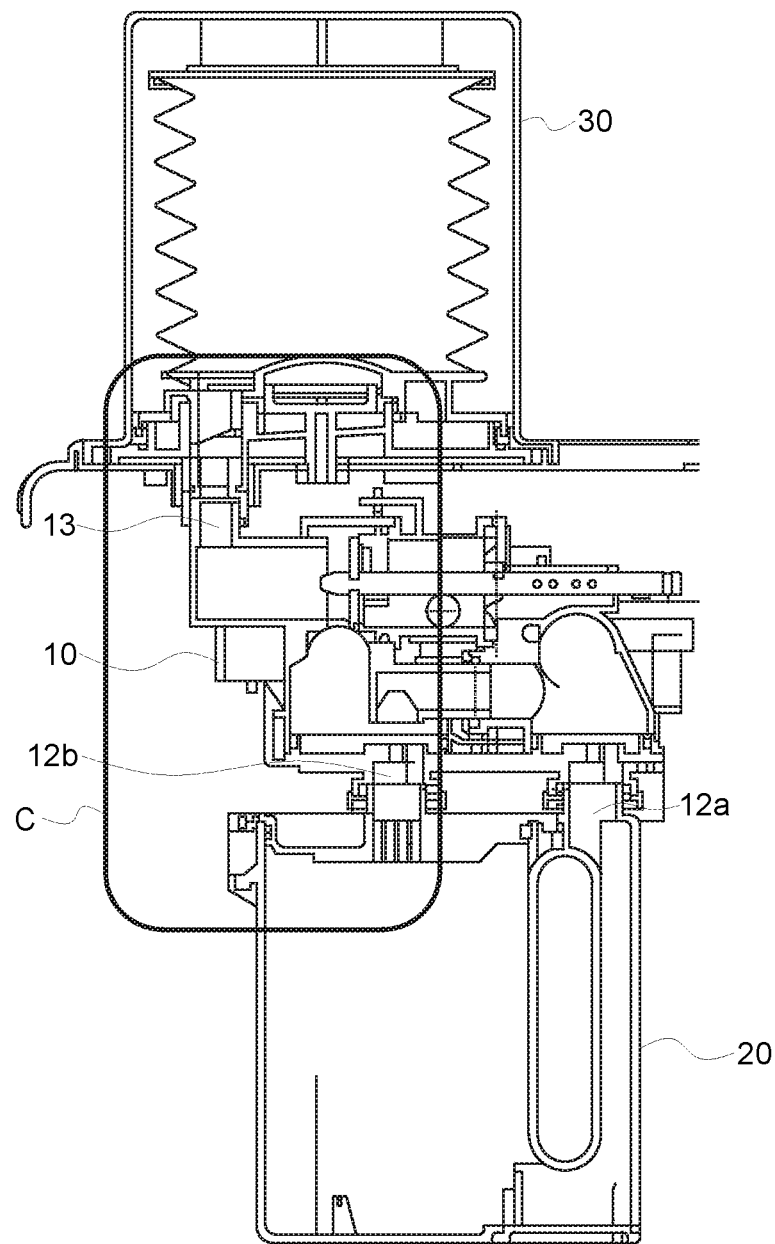
Figure 6:
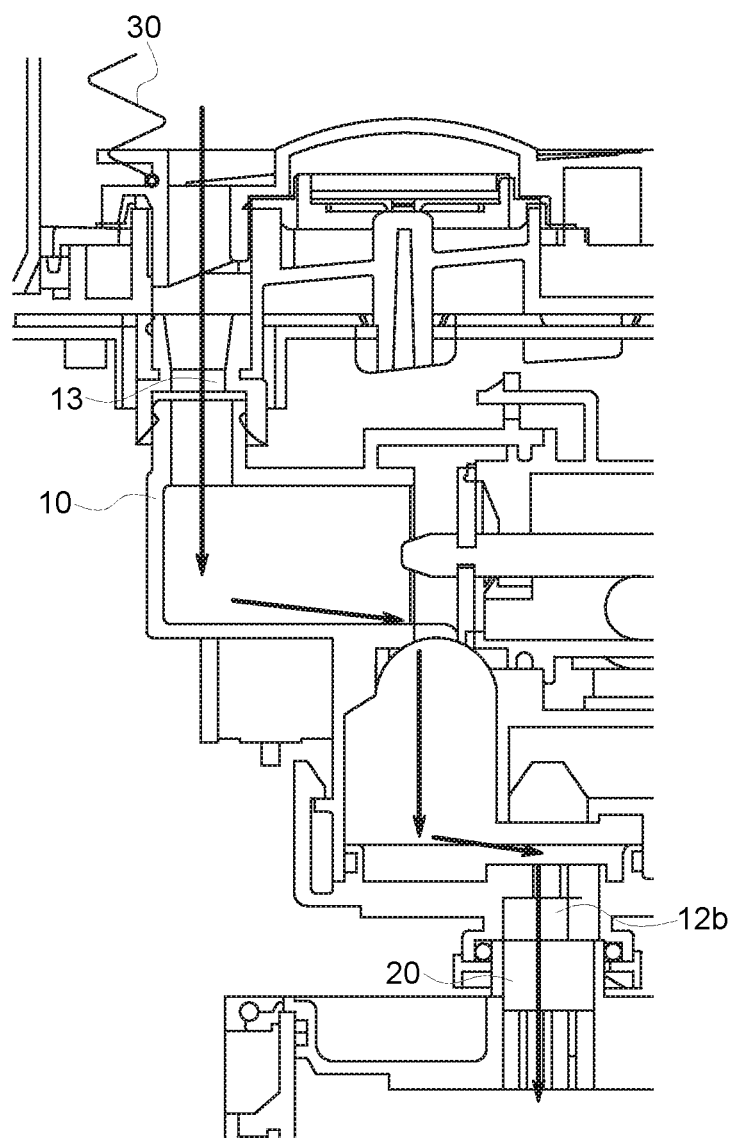
FIG. 6 is an enlarged view of part C in FIG. 5.
Figure 7:
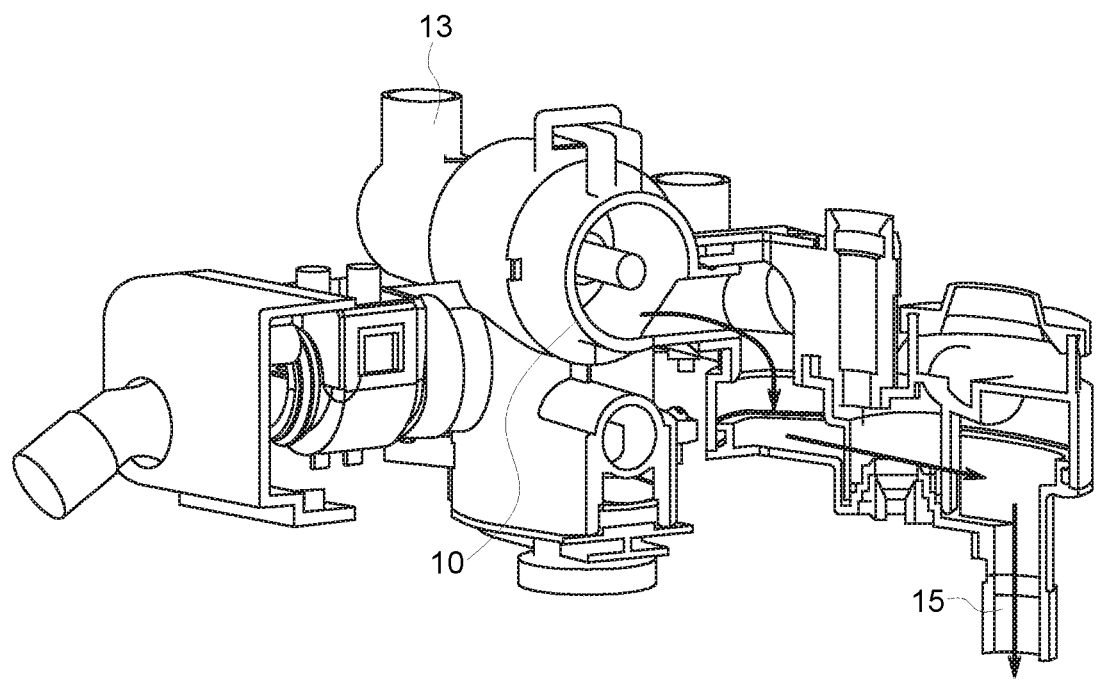

FIGS. 1, 3, 5 and 7 are structural views of a breathing system of an anesthesia machine according to an embodiment of the present disclosure; FIG. 2 is an enlarged view of part A in FIG. 1; FIG. 4 is an enlarged view of part B in FIG. 3; FIG. 6 is an enlarged view of part C in FIG. 5. FIGS. 1, 2 show an inspiratory branch of the breathing system for the anesthesia machine. FIGS. 3, 4 show an expiratory branch of the breathing system for the anesthesia machine. FIGS. 5, 6 show a passage from a bellow to a $CO_2$ canister, and FIG. 7 shows a passage from an operation mode switch to an manual bag hose. As shown in FIGS. 1-7, the breathing system for the anesthesia machine includes an operation mode switch 10, a $CO_2$ canister 20, a bellows 30, a patient inspiratory branch 51 and a patient expiratory branch 54.

One skilled in the art shall understand that the operation mode switch 10 is used for controlling the switching between the automatic operation mode and the manual operation mode; the $CO_2$ canister 20 is used for absorbing $CO_2$ from the gas exhaled by the patient; the bellows 30 is used for delivering the fresh gas through the operation mode switch 10 to the patient inspiratory branch 51 when the patient is inhaling, and the patient expiratory branch 54 is used for discharging the gas exhaled by the patient through the operation mode switch 10 and the bellows 30.

The $CO_2$ canister 20 is disposed at the bottom of the breathing system for the anesthesia machine, so as to be able to collect the condensate water produced in the breathing system (e.g. water in the bellows 30 and the operation mode switch 10).

The operation mode switch 10 includes a vent 11 communicating with the patient inspiratory branch 51, a vent communicating with the $CO_2$ canister 20, a vent 13 communicating with the bellow 30, and a vent 14 communicating with the patient expiratory branch 54.

The $CO_2$ canister 20 is positioned below the operation mode switch 10, so as to collect the water flowing through the operation mode switch 10.

The $CO_2$ canister 20 is provided below the operation mode switch 10, and the operation mode switch 10 communicates with the patient inspiratory branch 51, the bellows 30, the patient expiratory branch 54, and further the $CO_2$ canister 20, such that the water flowing from the bellows 30, the patient inspiratory branch 51 and the patient expiratory branch 54 toward the operation mode switch 10, can finally flow into the $CO_2$ canister 20.

For example, as shown in FIGS. 2, 4, and 6, the condensate water generated in the breathing system for the anesthesia machine and flowing into the operation mode switch 10 (including the condensate water produced in the operation mode switch 10 and flowing from the bellows 30, the patient inspiratory branch 51 and the patient expiratory branch 54 into the operation mode switch 10) may flow under gravity, to the vent at the bottom of the operation mode switch 10, and further flow into the $CO_2$ canister 20.

In this way, the condensate water in the breathing system for the anesthesia machine can be discharged effectively, and the generation of bacteria can be prevented. Moreover, when a user replaces the soda lime within the $CO_2$ canister 20, the water retained in the $CO_2$ canister 20 may be dumped at the same time. This does not produce additional cost and eliminates the need for special water collecting cups which may be forgotten to be emptied and thereby leaving condensate water in the breathing system.

Optionally, in an embodiment of the present disclosure, in order to facilitate the water to flow smoothly toward the $CO_2$ canister at different positions of the operation mode switch 10, the vent communicating the operation mode switch 10 with the $CO_2$ canister 20 includes a first vent and a second vent, such as the vents 12a and 12b shown in FIG. 5.

Optionally, there is a top-to-bottom water passage in the operation mode switch 10 between the vent 13 communicating with the bellows 30 and the vent communicating with the $CO_2$ canister 20. Through the top-to-bottom water passage, the water in the bellows 30 and the operation mode switch 10 is able to flow more smoothly into the $CO_2$ canister without water detours.

For example, the direction of the arrow in FIG. 6 is, in an embodiment, the flowing direction of condensate water in the water passage between the vents 13 and 12b.

It can be seen from the direction of the arrow in FIG. 6, the top-to-bottom water passage may be stepped. The top-to-bottom water passage above may be designed to be other forms, provided that the forms avoid water detours and conform to the structure of the operation mode switch itself.

Optionally, the vent communicating with the $CO_2$ canister 20 is particularly disposed at the bottom of the operation mode switch 10, such that the $CO_2$ canister 20 is able to collect effectively the water flowing through the operation mode switch 10. In other embodiments, for instance, the vents 12a and 12b are disposed at sides like the lower-left corner or the lower-right corner, of the operation mode switch 10.

Further, the vent 13 communicating with the bellows 30 is disposed at the top of the operation mode switch 10, such that the water in the bellows 30 is able to flow into the operation mode switch 10, and into the $CO_2$ canister 20 through the operation mode switch 10.

As shown in FIG. 2, the vent 12a is close to the patient inspiratory branch 51. As shown in FIG. 4, the vent 12b is close to the patient expiratory branch 54. As shown in FIG. 6, in the embodiment of the present disclosure, the water in the bellows 30 flows into the $CO_2$ canister 20 via the vent 12b.

The expressions "the vent 12a is close to the patient inspiratory branch 51" and "the vent 12b is close to the patient expiratory branch 54" mean that comparing the patient inspiratory branch 51 with the patient expiratory branch 54, the vent 12a is closer to the patient inspiratory branch 51 and the vent 12b is closer to the patient expiratory branch 54; or mean that comparing the vent 11 communicating with the patient inspiratory branch 51 with the vent 14 communicating with the patient expiratory branch 54, the vent 12a is closer to the vent 11 while the vent 12b is closer to the vent 14.

The breathing system for the anesthesia machine of the present disclosure further includes a first gas flow sensor 41 provided in the patient inspiratory branch 51 and a second gas flow sensor 44 provided in the patient expiratory branch 54.

The patient inspiratory branch 51 is particularly provided with an inhaling valve 60 for opening and closing the patient inspiratory branch 51, and the patient expiratory branch 54 is provided with an exhaling valve 70 for opening and closing the patient expiratory branch 54.

As shown in FIG. 2, the first gas flow sensor 41 is provided at one end of the patient inspiratory branch 51 communicating with the operation mode switch 10. The operation mode switch 10 has a water passage from the first gas flow sensor 41 to the vent 12a of the operation mode switch 10, that is, as shown by the arrow in the right direction in FIG. 2, the water passage from the right of the first gas flow sensor 41 to the vent 12a, and finally to the $CO_2$ canister 20. In the patient inspiratory branch 51, there is a water passage from the first gas flow sensor 41 to the end of the patient inspiratory branch 51 not communicating with the operation mode switch 10, that is, as shown by the arrow in the left direction in FIG. 2, the water passage from the left of the first gas flow sensor 41 to one end of the patient inspiratory branch 51 away from the vent 11, and finally to the patient inhaling hose (not shown).

As shown in FIG. 4, the second gas flow sensor 44 is provided at one end of the patient expiratory branch 54 communicating with the operation mode switch 10. The operation mode switch 10 has a water passage from the second gas flow sensor 44 to the vent 12b of the operation mode switch 10, that is, as shown by the arrow in the left direction in FIG. 4, the water passage from the left of the second gas flow sensor 44 to the vent 12b, and finally to the $CO_2$ canister 20. In the patient expiratory branch 54, there is a water passage from the second gas flow sensor 44 to the end of the patient expiratory branch 54 not communicating with the operation mode switch 10, that is, as shown by the arrow in the right direction in FIG. 4, the water passage from the right of the second gas flow sensor 44 to one end of the patient expiratory branch 54 away from the operation mode switch 10, and finally to the patient exhaling hose (not shown).

In the aforementioned design way, both the gas flow sensors may be provided on the highest level of the two water flowing direction (for example, the two water passages at the right and left sides of the first gas flow sensor 41 in FIG. 2, and the two water passages at the right and left sides of the second gas flow sensor 44 in FIG. 4), such that the condensate water at the gas flow sensors may flow respectively in two opposite directions, into the patient breathing hose or the $CO_2$ canister 20, and further it may be discharged via the patient breathing hose or the $CO_2$ canister, so as to avoid the impact of the accumulated water near the gas flow sensor on the very gas flow sensor.

In addition, it can be seen from FIGS. 2 and 4 that in the embodiment of the present disclosure, both the water passage from the first gas flow sensor 41 to the vent 12a of the operation mode switch 10, and the water passage from the second gas flow sensor 44 to the vent 12b of the operation mode switch 10 are stepped from the above to the below, which is beneficial to provide direct water drainage.

Further, the first gas flow sensor 41 has a membrane 41a and the second gas flow sensor 44 has a membrane 44a, and each of the membrane 41a and the membrane 44a does not contact with the inner wall at the bottom of the patient inspiratory branch 51 and the patient expiratory branch 54 respectively.

In this way, the problem of incorrect measured results of the gas flow sensor caused by the contact and interference of its valve with water, can be avoided.

As shown in FIGS. 1-4, owing to that the first gas flow sensor 41 is provided at one end of the patient inspiratory branch 51 communicating with the operation mode switch 10, the second gas flow sensor 44 is provided at one end of the patient expiratory branch 54 communicating with the operation mode switch 10, and in the embodiment of the present disclosure, the vents 11 and 14 communicating with the patient inspiratory branch 51 and the patient expiratory branch 54 are disposed at sides of the operation mode switch 10, hence the impact of the water flowing downwards from the top of the operation mode switch 10 on the gas flow sensors can be avoided.

The breathing system for the anesthesia machine of the present disclosure further includes an oxygen concentration sensor 80, which communicates with the operation mode switch 10 and the patient inspiratory branch 51, and is higher in position than the operation mode switch 10 and the patient inspiratory branch 51. In this way, the problem of incorrect measured results of the oxygen concentration sensor 80 caused by the condensate water in the breathing system for the anesthesia machine, can be avoided.

Optionally, as shown in FIG. 7, the operation mode switch 10 may further include a vent 15 communicating with an manual breathing bag connected by a gas hose (not shown). The skilled in the art shall understand that this hose is used for communicating with the manual breathing bag for providing the patient with gas available for patient inhaling when the operation mode switch 10 is switched into a manual bag ventilation mode. The above-mentioned vent 15 is particularly disposed at the bottom of the operation mode switch 10, such that the manual bag hose is able to collect the water flowing from the operation mode switch 10. The arrow in FIG. 7 is, in an embodiment, the direction of the condensate water flowing through the operation mode switch 10 to the vent 15 (finally flowing to the manual bag hose and discharged therefrom).

As a result, in the manual mode, a portion of the water in the anesthesia machine may still flow through the vent 12a or 12b to the $CO_2$ canister 20, and another portion of the water may, under gravity, flow through the vent 15 and into the manual bag hose, and finally be discharged from the manual bag hose. In this way, the condensate water can be effectively discharged from the respiratory system for anesthesia machine, the generation of bacteria will be avoided, no additional cost is produced and no water collecting cup is needed.

Although some exemplary embodiments have been described as mentioned above, it should be understood that various modifications may still be made. For example, if the described techniques are carried out in different orders, and/or if the components of the described system, architecture, device or circuit are combined in different ways and/or replaced or supplemented by additional components or equivalents thereof, proper results can still be achieved. Accordingly, other embodiments are also falling within the protection scope of the claims.

What is claimed is:

1. A breathing system for an anesthesia machine, comprising an operation mode switch, a $CO_2$ canister, a bellows, a patient inspiratory branch and a patient expiratory branch, wherein the operation mode switch comprises an inspiratory vent communicating with the patient inspiratory branch, an expiratory vent communicating with the patient expiratory branch, a bellows vent communicating with the bellows, and a $CO_2$ vent communicating with the $CO_2$ canister, and the $CO_2$ canister is positioned below the operation mode switch, so as to collect water flowing through the operation mode switch, wherein the $CO_2$ vent communicating with the $CO_2$ canister is disposed at a bottom of the operation mode switch, such that the $CO_2$ canister collects the water flowing through the operation mode switch, wherein the bellows vent communicating with the bellows is disposed at a top of the operation mode switch, such that water in the bellows flows into the operation mode switch, and into the $CO_2$ canister through the operation mode switch.

2. The breathing system of claim 1, wherein the $CO_2$ vent communicating with the $CO_2$ canister comprises a first vent close to the patient inspiratory branch and a second vent close to the patient expiratory branch, the water in the bellows flows into the $CO_2$ canister via the second vent.

3. The breathing system of claim 2, further comprising:
a first gas flow sensor provided at one end of the patient inspiratory branch communicating with the operation mode switch; and
a second gas flow sensor provided at one end of the patient expiratory branch communicating with the operation mode switch, wherein:
the operation mode switch has a first water passage from the first gas flow sensor to the first vent, and the patient inspiratory branch has a second water passage from the first gas flow sensor to the end of the patient inspiratory branch not communicating with the operation mode switch;
the operation mode switch has a third water passage from the second gas flow sensor to the second vent, and the patient expiratory branch has a fourth water passage from the second gas flow sensor to the end of the patient expiratory branch not communicating with the operation mode switch.

4. The breathing system of claim 3, wherein the inspiratory vent communicating with the patient inspiratory branch and the expiratory vent communicating with the patient expiratory branch are disposed at sides of the operation mode switch.

5. The breathing system of claim 3, wherein first water passage from the first gas flow sensor to the first vent and third water passage from the second gas flow sensor to the second vent are stepped top-to-bottom water passages.

6. A breathing system for an anesthesia machine, comprising an operation mode switch, a $CO_2$ canister, a bellows, a patient inspiratory branch and a patient expiratory branch, wherein the operation mode switch comprises an inspiratory vent communicating with the patient inspiratory branch, an expiratory vent communicating with the patient expiratory branch, a bellows vent communicating with the bellows, and a $CO_2$ vent communicating with the $CO_2$ canister, and the $CO_2$ canister is positioned below the operation mode switch, so as to collect water flowing through the operation mode switch, wherein the operation mode switch further includes a bag hose vent communicating with a manual bag hose, wherein the bag hose vent is disposed at a bottom of the operation mode switch, such that the manual bag hose collects water flowing from the operation mode switch.

7. A method for discharging water for an anesthesia machine including an operation mode switch, a $CO_2$ canister, a bellows, a patient inspiratory branch and a patient expiratory branch, the method comprising:
providing, at the operation mode switch, an inspiratory vent communicating with the patient inspiratory branch;
providing, at the operation mode switch, an expiratory vent communicating with the patient expiratory branch;
providing, at the operation mode switch, a bellows vent communicating with the bellows;
providing, at the operation mode switch, a $CO_2$ vent communicating with the $CO_2$ canister, wherein the $CO_2$ canister is positioned below the operation mode switch, and
collecting, at the $CO_2$ canister, water flowing through the operation mode switch, wherein the $CO_2$ vent communicating with the $CO_2$ canister is disposed at a bottom of the operation mode switch, such that the $CO_2$ canister collects the water flowing through the operation mode switch, wherein the bellows vent communicating with the bellows is disposed at a top of the operation mode switch, such that water in the bellows flows into the operation mode switch, and into the $CO_2$ canister through the operation mode switch.

8. The method of claim 7, wherein the $CO_2$ vent communicating with the $CO_2$ canister comprises a first vent close to the patient inspiratory branch and a second vent close to the patient expiratory branch, the water in the bellows flows into the $CO_2$ canister via the second vent.

9. The method of claim 8, further comprising:
providing a first gas flow sensor at one end of the patient inspiratory branch communicating with the operation mode switch; and
providing a second gas flow sensor at one end of the patient expiratory branch communicating with the operation mode switch, wherein:
the operation mode switch has a first water passage from the first gas flow sensor to the first vent, and the patient inspiratory branch has a second water passage from the first gas flow sensor to the end of the patient inspiratory branch not communicating with the operation mode switch;
the operation mode switch has a third water passage from the second gas flow sensor to the second vent, and the patient expiratory branch has a fourth water passage from the second gas flow sensor to the end of the patient expiratory branch not communicating with the operation mode switch.

10. The method of claim 9, wherein the inspiratory vent communicating with the patient inspiratory branch and the expiratory vent communicating with the patient expiratory branch are disposed at sides of the operation mode switch.

11. The method of claim 9, wherein first water passage from the first gas flow sensor to the first vent and third water passage from the second gas flow sensor to the second vent are stepped top-to-bottom water passages.

12. A method for discharging water for an anesthesia machine including an operation mode switch, a $CO_2$ canister, a bellows, a patient inspiratory branch and a patient expiratory branch, the method comprising:
providing, at the operation mode switch, an inspiratory vent communicating with the patient inspiratory branch;
providing, at the operation mode switch, an expiratory vent communicating with the patient expiratory branch;
providing, at the operation mode switch, a bellows vent communicating with the bellows;
providing, at the operation mode switch, a $CO_2$ vent communicating with the $CO_2$ canister, wherein the $CO_2$ canister is positioned below the operation mode switch, and
collecting, at the $CO_2$ canister, water flowing through the operation mode switch, wherein the anesthesia machine further comprises a manual bag hose, the method further comprising:
providing, at the operation mode switch, a bag hose vent communicating with the manual bag hose, wherein the bag hose vent is disposed at the bottom of the operation mode switch; and
collecting, at the manual bag hose, water flowing from the operation mode switch.

* * * * *